United States Patent [19]

Kongsamut et al.

[11] Patent Number: 5,356,910
[45] Date of Patent: Oct. 18, 1994

[54] USE OF N-(PYRIDINYL)-1H-INDOL-1-AMINES FOR THE TREATMENT OF OBSESSIVE-COMPULSIVE DISORDER

[75] Inventors: Sathapana Kongsamut, Madison; Craig P. Smith, Hillsborough; Ann T. Woods, High Bridge, all of N.J.

[73] Assignee: Hoechst-Roussel Pharmaceuticals Inc., Somerville, N.J.

[21] Appl. No.: 92,848

[22] Filed: Jul. 19, 1993

[51] Int. Cl.$^5$ .................. A61K 31/44; A61K 31/40; A61K 31/405
[52] U.S. Cl. .................. 514/339; 514/333; 514/412; 514/414; 514/415; 514/419
[58] Field of Search ............. 514/339, 414, 412, 415, 514/419, 333

[56] References Cited

U.S. PATENT DOCUMENTS

| | | |
|---|---|---|
| 4,880,822 | 11/1989 | Effland et al. ............ 514/339 |
| 4,970,218 | 11/1990 | Effland et al. ............ 514/339 |
| 5,179,099 | 1/1993  | Effland et al. ............ 514/339 |

Primary Examiner—Marianne M. Cintins
Assistant Examiner—K. Weddington
Attorney, Agent, or Firm—Tatsuya Ikeda

[57] ABSTRACT

There is disclosed a method of alleviating obsessive compulsive disorders which comprises administration of an effective amount of a compound of the formula.

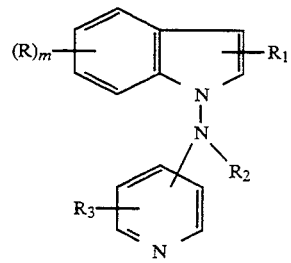

where
m is 1 or 2;
R is H, halogen, loweralkyl, loweralkoxy, aryl-loweralkoxy, hydroxy, nitro, amino, loweralkylamino or diloweralkylamino;
$R_1$ is H or loweralkyl;
$R_2$ is H or loweralkyl; and
$R_3$ is H, halogen or loweralkyl.

20 Claims, No Drawings

USE OF N-(PYRIDINYL)-1H-INDOL-1-AMINES FOR THE TREATMENT OF OBSESSIVE-COMPULSIVE DISORDER

The present invention relates to a method of alleviating obsessive compulsive disorders which comprises administration of an effective amount of a compound of the formula (I),

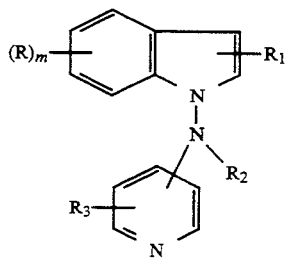

where
m is 1 or 2;

R is H, halogen, loweralkyl, loweralkoxy, aryl-loweralkoxy, hydroxy, nitro, amino, loweralkylamino or diloweralkylamino;

$R_1$ is H or loweralkyl;

$R_2$ is H or loweralkyl; and $R_3$ is H, halogen or loweralkyl, or a pharmaceutically acceptable acid addition salt thereof.

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

The compounds of Formula I used in the method of this invention can be prepared by utilizing the synthetic scheme described below where the parameters R, $R_1$, $R_2$, $R_3$ and m have the respective meanings as defined above unless otherwise indicated.

STEP A

An N-aminoindole of Formula II (where $R_4$ is hydrogen, loweralkyl, loweralkoxy, arylloweralkoxy or benzyloxy) is allowed to react with a chloro- or fluoropyridine of Formula III (where X is chlorine or fluorine) to afford a compound of Formula Ia.

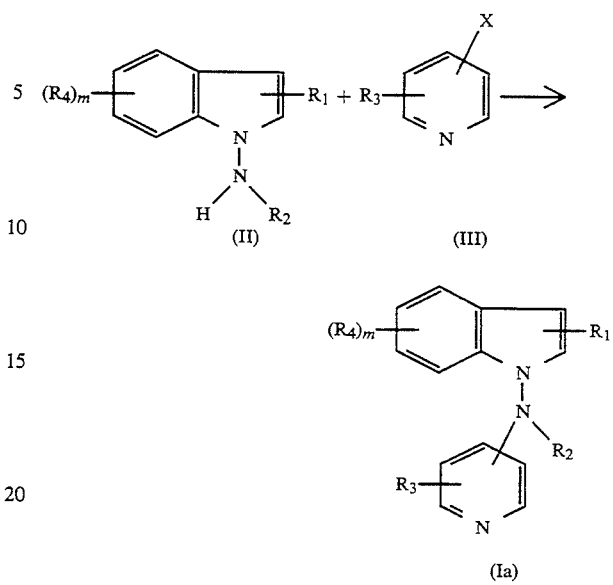

Said reaction is typically conducted in an ethereal solvent such as bis(2-methoxyethyl)ether, diethyl ether, dimethoxy ether, dioxane or tetrahydrofuran or polar aprotic solvent such as dimethylformamide, dimethylacetamide, N-methyl-2-pyrrolidone, hexamethylphosphoramide or dimethylsulfoxide or protic solvent such as ethanol or isopropanol at a temperature of between about 20° C. and 150° C.

STEP B

As an alternative to STEP A, a compound of Formula Ib obtained above is allowed to react with a strong base such as sodium hydride in a suitable solvent such as a polar aprotic solvent including dimethylformamide, dimethylsulfoxide and ethereal solvents or an aromatic hydrocarbon at a temperature of between about −10° and 50° C., preferably 0°–25° C. to form the corresponding anion and the latter is allowed to react with a loweralkyl chloride or bromide of the formula $R_2$-Hal (where Hal is chlorine or bromine, and $R_2$ is loweralkyl) or a diloweralkylsulfate of the formula $(R_2O)_2SO_2$ at a temperature of between about −10° and 80° C., preferably between 0° and 25° C. to afford a compound of Formula Ia (where $R_2$ is loweralkyl).

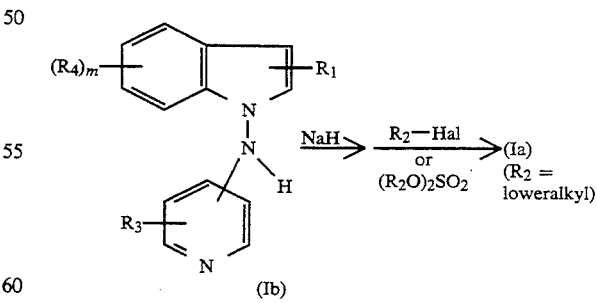

STEP C

Where compounds of Formula I in which the group R is amino, loweralkylamino or diloweralkylamino are desired, one starts out with a compound of Formula Ic obtained from STEP A or STEP B and converts the nitro group present on the benzene ring moiety into an amino group, loweralkylamino group or diloweralkylamino group by utilizing synthetic methods known to the art.

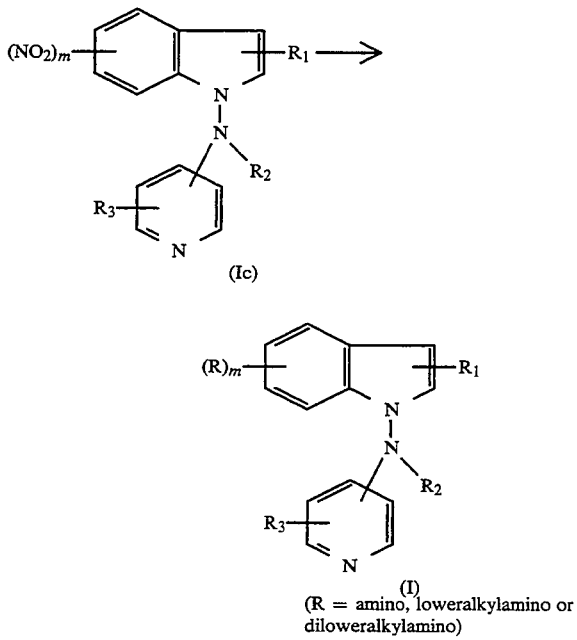

(R = amino, loweralkylamino or diloweralkylamino)

STEP D

Where compounds of Formula I where the group R is hydroxy are desired, one starts out with a compound of Formula Id obtained from STEP A or STEP B and converts the benzyloxy group to a hydroxy group in a routine manner known to the art to obtain a compound of Formula Ie.

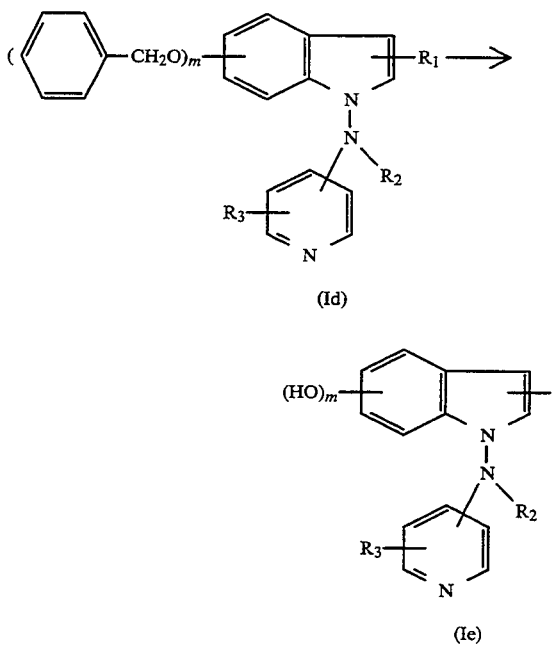

The compounds of Formula I are useful for alleviating obsessive compulsive disorders. This utility can be ascertained on the basis of a protocol described below in detail which is referred to as Schedule-Induced Polydipsia in Rats (SIP).

SCHEDULE-INDUCED POLYDIPSIA IN RATS

PURPOSE:

This assay was established to evaluate the activity of serotonin re-uptake inhibitors that may have efficacy in obsessive compulsive disorder (OCD). Food deprived rats exposed to a fixed time feeding schedule and allowed free access to water develop an excessive drinking behavior known as polydipsia. This schedule-induced polydipsia (SIP) can not be explained in terms of a physiological deficit due to water deprivation. Furthermore, this excessive drinking is an irrelevant activity since it offers no benefit or reward to the rat (Falk, 197 1, Robbins & Koob, 1980). To date the serotonin re-uptake inhibitors that reduce compulsive behaviors in OCD also reduced schedule-induced polydipsic behavior (Goodman, 1990; Insel et al., 1990; Rapoport, 1991; Woods et al., 1993).

METHODS:

Male Wistar rats (Charles River) weighing 180–220 grams were group housed and maintained in accordance with the "NIH Guide to Care and Use of Laboratory Animals" (National Institute of Health Care Publications, No. 85-23, revised 1985) with a 12 hour light/12 hour dark cycle and allowed free access to food and water. After several days of acclimation, the rats were transferred to individual cages and placed on a restricted diet which maintained 80% of their free feeding body weight for at least 3 days prior to the start of the study. This is accomplished by feeding the rats four pellets of food per day, each pellet weighing 4 grams. At this time the rats are permanently marked with an identification number either by tatoo or ear tag since they are constantly being handled in large groups. To induce polydipsia, rats were placed in operant chambers housed in sound attenuated boxes where a pellet dispenser automatically dispensed two 45 mg (Noyes) pellets on a fixed-time schedule of once every 60 seconds (abbreviated below as "FT-60 sec. schedule") over a 150 minute test session. Water was available at all times in the operant chambers. On the days that the rats received food in the chambers, they were not given the four 4-gram pellets. After four weeks (Monday through Friday) of exposure to the FT-60 sec. feeding schedule, approximately 80% of the rats met a pre-determined criterion for water consumption (greater than 60 mls of water per session) and were considered polydipsic. The rats were randomly assigned to a group so that each dose group had a comparable mean and S.E.M. Each group was also randomized as well as possible with regard to the time of day the tests were run and the chambers in which the tests were run. Rats (N=8) were administered, intraperitoneally (IP), vehicle or the appropriate compound daily. Once dosing commenced, the rats were tested in the operant chambers once a week to assess SIP. A 60 minute pretreatment was utilized on test days. Studies were done chronically for a duration of 29 days. A reduction of polydipsia was taken as indicative of potential for reduction of symptoms of obsessive compulsive disorder.

These experiments were analyzed by the Mann Whitney U-Test.

DRUGS:

Compounds were either dissolved or suspended in distilled water plus a drop of Tween 80 and injected IP in a dosage volume of 1 ml/kg. The final volume was prepared to account for salt content and the dosage was expressed as 100% base.

REFERENCES:

1. Falk, J., (1971): The Nature and Determinants of Adjunctive Behavior, *Physiology and Behavior.* 6, 577–588.
2. Goodman W. K., Price, L. H., Delgado D. L., Palumbo, J., Krystal, J. H., Nagy, L. M., Rassmussen, S. A., Heninger, G. R., Charney, D. S., (1990): Specificity of Serotonin Re-Uptake Inhibitors in the Treatment of OCD, *Arch. Gen. Psych.* 47:577–585.
3. Insel, T. R., Zohar, J., Benkelfat, C., Murphy, C., (1990): Serotonin in Obsessions, Compulsions, and the control of Aggressive Impulses, *Annals NY Acad., Sci.* 600:574–586.
4. Pitman, K. K. (1989): Animal Models of Compulsive Behavior, *Biol. Psych.* 26:189–198.
5. Rapoport, J. L., (1991): Recent Advances in Obsessive-Compulsive Disorder, *Neuropsychopharmacology.* 5,1–10.
6. Woods, A., Smith, C., Szewczak, M., Dunn, R. W., Comfeldt, M., (1993): Selective Serotonin Re-Uptake Inhibitors Decrease Schedule-Induced Polydipsia in Rats: A Potential Model for Obsessive Compulsive Disorder, *Psychopharmacology* in press.

Results of the above protocol are presented in Table 1 for a representative compound of this invention and two reference compounds.

TABLE 1

| Polydipsia in Rats | |
|---|---|
| Compound | Dose (mg/kg, i.p. per day) |
| N-(3-fluoro-4-pyridinyl)-N-propyl-3-methyl- 1H-indol-1-amine | Active at 15 |
| N-(4-pyridinyl)N-propyl-1H-indol-1-amine HCl | Active at 10 |
| (Reference Compounds) | |
| Clomipramine | Active at 5 |
| Fluoxetine | Active at 5 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterorex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are 2prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of compounds which can be used for the method of this invention for alleviating obsessive compulsive disorders include:

N-(4-pyridinyl)-1H-indol-1-amine;
N-methyl-N-(4-pyridinyl)-1H-indol-1-amine;
N-ethyl-N-(4-pyridinyl)-1H-indol-1-amine;
N-propyl-N-(4-pyridinyl)-1H-indol-1-amine;
5-methoxy-N-propyl-N-(4-pyridinyl)-1H-indol-1-amine;
3-ethyl-N-methyl-N-(4-pyridinyl)-1H-indol-1-amine;
5-chloro-N-(4-pyridinyl)-1H-indol-1-amine;
5-chloro-N-propyl-N-(4-pyridinyl)-1H-indol-1-amine;

5-bromo-N-(4-pyridinyl)-1H-indol-1-amine;
5-bromo-N-methyl-N-(4-pyridinyl)-1H-indol-1-amine;
5-bromo-N-propyl-N-(4-pyridinyl)-1H-indol-1-amine;
5-Nitro-N-(4-pyridinyl)-1H-indol-1-amine;
N-Methyl-5-nitro-N-(4-pyridinyl)-1H-indol-1-amine;
3-Methyl-N-(4-pyridinyl)-1H-indol-1-amine;
3-Methyl- N-propyl-N-(4-pyridinyl)-1H-indol-1-amine;
N-(3-Fluoro-4-pyridinyl)-3-methyl-1H-indol-1-amine;
N-(3-Fluoro-4-pyridinyl)-N-propyl-3-methyl-1H-indol-1-amine;
N-(3-Fluoro-4-pyridinyl)-N-propyl-1H-indol-1-amine;
2-Methyl-N-(4-pyridinyl)-1H-indol-1-amine;
N-(3-Methyl-4-pyridinyl)-1H-indol-1-amine;
N-(3-Methyl-4-pyridinyl)-N-propyl-1H-indol-1-amine;
N-(3-Fluoro-4-pyridinyl)-1H-indol-1-amine;
N-(3-Chloro-4-pyridinyl)-1H-indol-1-amine;
N-(3-Fluoro-4-pyridinyl)-2-methyl-1H-indol-1-amine;
N-(3-Chloro-4-pyridinyl)-3-methyl-1H-indol-1-amine;
3-Ethyl-N-propyl-N-(4-pyridinyl)-1H-indol-1-amine;
N-Butyl-N-(4-pyridinyl)-1H-indol-1-amine;
N-(2-Methylpropyl)-N-(4-pyridinyl)-1H-indol-1-amine;
N-Pentyl-N-(4-pyridinyl)-1H-indol-1-amine;
N-(2-Methylpropyl)-N-(4-pyridinyl)-1H-indol-1-amine;
N-(2-Methylethyl)-N-(4-pyridinyl)-1H-indol-1-amine;
2-Methyl-N-propyl-N-(4-pyridinyl)-1H-indol-1-amine;
N-(3-Chloro-4-pyridinyl)-N-propyl-1H-indol-1-amine;
N-(3-Fluoro-4-pyridinyl)-2-methyl-N-propyl-1H-indol-1-amine;
N-(3-Chloro-4-pyridinyl)-3-methyl-N-propyl-1H-indol-1-amine;
5 -Hydroxy-N-(4-pyridinyl)-1H-indol-1-amine;
5-Hydroxy-N-propyl-N-(4-pyridinyl)-1H-indol-1-amine;
3-Methyl-N-(3-methyl-4-pyridinyl)-1H-indol-1-amine;
3-Methyl-N-(3-methyl-4-pyridinyl)-N-propyl-1H-indol-1-amine;
2- Methyl-N-(3-methyl-4-pyridinyl)-1H-indol-1-amine; and
2-Methyl-N-(3-methyl-4-pyridinyl)-N-propyl-1H-indol-1 -amine;

The following examples are presented in order to illustrate the synthesis of various compounds which can be used for the method of this invention.

EXAMPLE 1

N-(4-Pyridinyl)-1H-indol-1-amine maleate

A solution of 1H-indol-1-amine (30 g), 4-chloropyridine hydrochloride (34 g) and pyridine (18 g) in 250 ml of isopropanol was stirred at 85° for 1.5 hours, and thereafter cooled, stirred and ice-water, basified with sodium carbonate and extracted with dichloromethane. The organic extract was washed with water and saturated sodium chloride solution, was dried over anhydrous magnesium sulfate, filtered and concentrated to a dark oil. This oil was purified by flash chromatography (silica, ethyl acetate) and thereafter by column chromatography (alumina, ether) to give 24 g of oil. A 3.6 g sample was purified by high performance liquid chromatography (HPLC hereafter) (silica, ethyl acetate) to give 3.5 g of oil. This oil was converted to the maleate salt and recrystallized twice from methanol/ether to give 3.8 g of needles, m.p. 145°-146° (dec.).

ANALYSIS:

Calculated for $C_{13}H_{11}N_3 \cdot C_4H_4O_4$: 62.75%C 4.65%H 12.92%N

Found: 62.62%C 4.81%H 12.73%N

EXAMPLE 2

N-Methyl-N-(4-pyridinyl)-1H-indol-1-amine maleate

A solution of N-(4-pyridinyl)-1H-indol-1-amine (7.4 g) in 30 ml of dimethylformamide was added to an ice-cooled suspension of NaH (1.6 g of 60% NaH dispersion in mineral oil was washed with hexanes, the liquid portion was decanted and the residual solid was dispersed in 10 ml of dimethylformamide). After anion formation, a solution of dimethylsulfate (5 g) in 10 ml of dimethylformamide was added. After one hour of stirring at ambient temperature, the reaction mixture was stirred with ice-water and extracted with ether. The organic extract was washed with water and saturated sodium chloride solution, was dried over anhydrous magnesium sulfate, filtered and concentrated to 8 g of oil. This oil was purified by flash chromatography (silica, ethyl acetate), column chromatography (alumina, ether) and HPLC (silica, ethyl acetate) to give 2.9 g of oil. This oil was converted to the maleate salt and was recrystallized twice from methanol/ether to give 2.1 g of crystals, m.p. 103°-104°.

ANALYSIS:

Calculater for $C_{14}H_{13}N_3 \cdot C_4H_4O_4$: 63.70%C 5.05%H 12.39%N

Found: 63.36%C 4.93%H 12.39%N

EXAMPLE 3

N-Ethyl-N-(4-pyridinyl)-1H-indol-1-amine maleate

To an ice-cooled suspension of sodium hydride (1.7 g of 60% NaH dispersion in mineral oil was washed with hexanes, the liquid was decanted and the residual solid was dispersed in 5 ml of dimethylformamide) was slowly added a solution of N-(4-pyridinyl)- 1H-indol-1-amine (7.6 g) in 25 ml of dimethylformamide. After anion formation, a solution of diethyl sulfate (6.4 g) in 10 ml of dimethylformamide was slowly added. After one hour, the mixture was stirred with ice-water and extracted with ethyl acetate. The organic extract was washed with water and saturated sodium chloride solution, was dried over anhydrous magnesium sulfate, filtered and concentrated to 11 g of oil. This oil was purified by flash chromatography (silica, ethyl acetate) to give 6.2 g of oil. This oil was purified by column chromatography (alumina, ether) to give 6 g of oil. A 3 g sample was convened to the maleate salt and recrystallized from ethanol/ether and thereafter from methanol/ether to give 2.7 g of crystals, m.p. 119°-120°.

ANALYSIS:

Calculated for $C_{15}H_{15}N_3 \cdot C_4H_4O_4$: 64.58%C 5.42%H 11.89%N

Found: 64.27%C 5.49%H 12.11% N

EXAMPLE 4

Part A: N-Propyl-N-(4-pyridinyl)-1H-indol-1-amine maleate

A solution of N-(4-pyridinyl)-1H-indol-1-amine (6 g) in 25 ml of dimethylformamide was slowly added to an ice-cooled suspension of NaH (1.3 g of 60% NaH dispersion in mineral oil was washed with hexanes, the liquid was decanted and the residual solid was dispersed in 5 ml of dimethylformamide). After anion formation, a solution of 1-bromopropane (4 g) in 5 ml of dimethylformamide was added. After one hour of stirring at ambient temperature, the reaction mixture was stirred with ice-water and extracted with dichloromethane. The organic extract was washed with water and saturated sodium chloride solution, was dried over anhydrous magnesium sulfate, filtered and concentrated to 8 g of oil. This oil was purified by HPLC (silica, ethyl acetate) and thereafter by column chromatography (alumina, ether) to give 6.4 g oil. This oil was converted to the maleate salt and recrystallized from methanol/ether to give 6.8 g of crystals, m.p. 115°–116°.

ANALYSIS:

Calculated for $C_{16}H_{17}N_3 \cdot C_4H_4O_4$: 65.38%C 5.76%H 11.44%N

Found: 65.26%C 5.71%H 11.34%N

Part B: N-Propyl-N-(4-pyridinyl)-1H-indol-1-amine hydrochloride

The free base oil was converted to the hydrochloride salt which was recrystallized from methanol; m.p. 212°–214°.

ANALYSIS:

Calculated for $C_{16}H_{17}N_3 \cdot HCl$: 66.78%C 6.30%H 14.60%N

Found: 66.77%C 6.39%H 14.59%N

EXAMPLE 5

5-Methoxy-N-propyl-N-(4-pyridinyl)-1H-indol-1-amine maleate

To an ice-cooled suspension of sodium hydride (0.5 g of 60% NaH dispersion in mineral oil was washed with hexanes, the liquid was decanted and the residual solid was dispersed in 5 ml of dimethylformamide) was slowly added a solution of 5-methoxy-N-(4-pyridinyl)-1H-indol-1-amine (2.3 g) in 20 ml of dimethylformamide. After anion formation, a solution of 1-bromopropane (1.4 g) in 5 ml of dimethylformamide was added. After one hour of stirring, the reaction mixture was stirred with ice-water and extracted with dicloromethane. The organic extract was washed with water and saturated sodium chloride solution, was dried over anhydrous magnesium sulfate, filtered and concentrated to 2.3 g of oil. This oil was purified by flash chromatography (silica, ethyl acetate) to give 2.1 g of oil. This oil was converted to the maleate salt in ethanol/ether to give 2.0 g of crystals, m.p. 138°–139°.

ANALYSIS:

Calculated for $C_{17}H_{19}N_3O \cdot C_4H_4O_4$: 63.46%C 5.83%H 10.58%N

Found: 63.26%C 5.77%H 10.47%N

EXAMPLE 6

N-Methyl-N-(4-pyridinyl)-1H-indol-1-amine-3-carboxaldehyde maleate

To ice-cooled dimethylformamide (4 g) was slowly added phosphorous oxychloride (7 g). After complex formation, a solution of N-methyl-N-(4-pyridinyl)-1H-indol-1-amine (5 g) in 50 ml of dichloroethane was added. After one hour of stirring at 85°, the reaction mixture was cooled, hydrolyzed with a solution of sodium acetate (5 g) in 25 ml of water, again cooled, basified with sodium carbonate and extracted with dichloromethane. The organic extract was washed with water and saturated sodium chloride solution, was dried over anhydrous magnesium sulfate, filtered and concentrated to 6 g of oil. This oil was purified by flash chromatography (silica, ethyl acetate) to give 4.6 g of oil. This oil was converted to the maleate salt and recrystallized from ethanol/ether and thereafter from methanol/ether to give 2.6 g of crystals, m.p. 162°–163° (dec.).

ANALYSIS:

Calculated for $C_{15}H_{13}N_3O \cdot C_4H_4O_4$: 62.12%C 4.66%H 11.44%N

Found: 61.71%C 4.62%H 11.14%N

EXAMPLE 7

N-Ethyl-N-(4pyridinyl)-1H-indol-1-amine-3-carboxaldehyde maleate

To ice-cooled dimethylformamide (2.2 g) was slowly added phosphorous oxychloride (4.5 g). After complex formation, a solution of N-ethyl-N-(4-pyridinyl)-1H-indol-1-amine (3.5 g) in 50 ml of dichloroethane was added. The mixture was stirred at 80° for one hour and thereafter hydrolyzed with a solution of sodium acetate (5 g) in 25 ml of water, cooled, basified with sodium carbonate and extracted with dichloromethane. The organic extract was washed with water and saturated sodium chloride solution, was dried over anhydrous magnesium sulfate, filtered and concentrated to 5 g of oil. This oil was purified by flash chromatography (silica, ethyl acetate) to give 3.5 g of oil. This oil was converted to the maleate salt and recrystallized from ethanol/ether and thereafter from methanol/ether to give 3 g of solid, m.p. 170°–17 1° (dec.).

ANALYSIS:

Calculated for $C_{16}H_{15}N_3O \cdot C_4H_4O_4$: 62.98%C 5.02%H 11.02%N

Found: 62.97%C 5.08%H 11.06%N

EXAMPLE 8

3-Ethenyl-N-methyl-N-(4-pyridinyl)-1H-indol-1-amine maleate

To an ice-cooled suspension of methyltriphenylphosphonium bromide (13 g) in 100 ml of anhydrous ether was added potassium t-butoxide (4 g). After phosphorane formation, a solution of N-ethyl-N-(4-pyridinyl)-1H-indol-1-amine-3-carboxaldehyde (7.5 g) in 50 ml of ether and 50 ml of tetrahydrofuran was added. After one hour of stirring, the reaction mixture was stirred with water and extracted with ether. The organic extract was washed with water and saturated sodium chloride solution, was dried over anhydrous magnesium sulfate, filtered and concentrated to 20 g of oil. This oil was purified by flash chromatography (silica, ethyl acetate) to give 7 g of oil. A 3.5 g sample was converted to the maleate salt in ethanol and recrystallized from methanol ether to give 3 g of crystals, m.p. 153°–154°.

ANALYSIS:

Calculated for $C_{16}H_{15}N_3 \cdot C_4H_4O_4$: 65.74%C 5.24%H 11.50%N

Found: 65.94%C 5.39%H 11.45%N

EXAMPLE 9

3-Ethyl-N-methyl-N-(4-pyridinyl)-1H-indol-1-amine hydrochloride

A solution of 3-ethenyl-N-methyl-N-(4-pyridinyl)-1H-indol-1-amine (5 g) in 250 ml of ethanol containing 0.5 g of platinum oxide was hydrogenated at 50 psi for one hour. The mixture was filtered and the filtrate was concentrated to 5 g of oil. This oil was purified by flash chromatography (silica, ethyl acetate) to give 3.5 g of oil. This oil was converted to the hydrochloride salt in ethanol/ether and recrystallized from methanol/ether to give 3.0 g of crystals, m.p. 262°(dec.).

ANALYSIS:

Calculated for $C_{16}H_{17}N_3 \cdot HCl$: 66.77%C 6.30%H 14.60%N

Found: 66.87%C 6.33%H 14.57%N

EXAMPLE 10

5-Chloro-N-(4-pyridinyl)-1H-indol-1-amine maleate

A solution of 5-chloro-1H-indol-1-amine (9 g), 4-chloropyridine hydrochloride (12 g) and pyridine (6.4 g) in 100 ml of isopropanol was stirred at reflux for one hour, cooled and stirred with ice-water, and the mixture was basified with sodium carbonate, extracted with dichloromethane and filtered. The organic extract was washed with water and saturated sodium chloride, was dried over anhydrous magnesium sulfate, filtered and concentrated to a dark oil. This oil was purified by flash chromatography (silica, ethyl acetate) to give 6.2 g of oil. This oil was converted to the maleate salt in methanol-ether to give 7 g of crystals, m.p. 148°–150°. A 2.6 g sample was recrystallized from methanol-ether to give 2.4 g of crystals, m.p. 150°–152° (dec.).

ANALYSIS:

Calculated for $C_{13}H_{10}ClN_3 \cdot C_4H_4O_4$: 56.75%C 3.92%H 11.68%N

Found: 56.71%C 4.00%H 11.62%N

EXAMPLE 11

5-Chloro-N-propyl-N-(4-pyridinyl)-1H-indol-1-amine maleate

A solution of 5-chloro-N-(4-pyridinyl)-1H-indol-1-amine (3.3 g) in 15 ml of dimethylformamide was slowly added to an ice-cooled suspension of sodium hydride (0.65 g of 60% oil dispersion was washed with hexanes) in 5 ml of dimethylformamide. After anion formation a solution of 1-bromopropane (2 g) in 5 ml of dimethylformamide was added. After one hour the reaction mixture was stirred with ice-water and extracted with dichloromethane. The organic extract was washed with water and saturated sodium chloride, was dried over anhydrous magnesium sulfate, filtered and concentrated to 5 g of oil. This oil was purified by flash chromatography (silica, ethyl acetate) to give 3.1 g of oil. This oil was converted to the maleate salt in ethanol-ether and thereafter recrystallized from methanol-ether to give 3.4 g of crystals, m.p. 130°.

ANALYSIS:

Calculated for $C_{16}H_{16}ClN_3 \cdot C_4H_4O_4$: 59.77%C 5.02%H 10.46%N

Found: 59.97%C 5.13%H 10.35N

EXAMPLE 12

5-Bromo-N-(47pyridinyl)-1H-indol-1-amine maleate

A solution of 5-bromo-1H-indol-1-amine (13 g), 4-chloropyridine hydrochloride (14 g) and pyridine (7.2 g) in 100 ml of isopropanol was stirred at reflux for one hour, cooled and stirred with ice-water, and thereafter the mixture was basified with sodium carbonate, extracted with dichloromethane and filtered. The organic extract was washed with water and saturated sodium chloride, was dried over anhydrous magnesium sulfate, filtered and concentrated to a dark oil. This oil was purified by flash chromatography (silica, ethyl acetate) to give 11 g of oil.. This oil was converted to the maleate salt in ethanol-ether to give 13 g of solid, m.p. 155°–157° (dec.). A three gram sample was recrystallized from methanol-ether to give 2.8 g of crystals, m.p. 161°–162° (dec.).

ANALYSIS:

Calculated for $C_{13}H_{10}BrN_3 \cdot C_4H_4O_4$: 50.51%C 3.49%H 10.40%N

Found: 50.46%C 3.56%H 10.40%N

EXAMPLE 13

5-Bromo-N-methyl-N-(4-pyridinyl)-1H-indol-1-amine maleate

A solution of 5-bromo-N-(4-pyridinyl)-1H-indol-1-amine (2.7 g) in 20 ml of dimethylformamide was slowly added to an ice-cooled suspension of sodium hydride (0.45 g of 60% oil dispersion was washed with hexanes) in 5 ml of dimethylformamide. After anion formation a solution of dimethylsulfate (1.4 g) in 5 ml of dimethylformamide was added. After one hour the reaction mixture was stirred with ice-water and extracted with dichloromethane. The organic extract was washed with water and saturated sodium chloride, was dried over anhydrous magnesium sulfate, filtered and concentrated to 2 g of oil. This oil was purified by flash chromatography (silica, ethyl acetate) to give 1.4 g of oil. This oil was converted to the maleate salt in ethanol-ether to give 1.2 g of crystals, m.p. 110°–111°.

ANALYSIS:

Calculated for $C_{14}H_{12}BrN_3 \cdot C_4H_4O_4$: 51.69%C 3.86%H 10.05%N

Found: 51.55%C 3.89%H 10.14%N

EXAMPLE 14

5-Bromo-N-propyl-N-(4-pyridinyl)-1H-indol-1-amine maleate

A solution of 5-bromo-N-(4-pyridinyl)-1H-indol-1-amine (4.9 g) in 25 ml of dimethylformamide was slowly added to an ice-cooled suspension of sodium hydride (0.8 g of 60% oil dispersion was washed with hexanes) in 5 ml of dimethylformamide. After anion formation a solution of 1-bromopropane (2.5 g) in 5 ml of dimethylformamide was added. After one hour the reaction mixture was stirred with ice-water and extracted with dichloromethane. The organic extract was washed with water and saturated sodium chloride, was dried over anhydrous magnesium sulfate, filtered and concentrated to 5 g of oil. This oil was purified by flash chromatography (silica, ethyl acetate) to give 4.5 g of oil. This oil was converted to the maleate salt in ethanol-ether to give 5.4 g of solid, m.p. 150°–152° (dec.). This solid was recrystallized from methanol-ether to give 4.8 g of crystals, m.p. 157°–158° (dec.).

ANALYSIS:

Calculated for $C_{16}H_{16}BrN_3 \cdot C_4H_4O_4$: 53.82% C 4.52% H 9.42% N

Found: 53.63%C 4.62%H 9.40%N

EXAMPLE 15

5-Nitro-N-(4-pyridinyl)-1H-indol-1-amine hydrochloride

A solution of 5-nitro-1H-indol-1-amine (4.5 g) and 4-chloropyridine hydrochloride (4.5 g) in 175 ml of isopropanol was stirred at reflux for two hours, another equivalent of 4-chloropyridine hydrochloride was added and the mixture was refluxed for two additional hours. The reaction mixture was then cooled, stirred with water, basified with sodium carbonate and extracted with ethyl acetate. The organic extract was washed with water and saturated sodium chloride solution, was dried (MgSO$_4$), filtered and concentrated to 9 g of dark oil. This oil was purified by flash chromatography (silica, ethyl acetate) to give 3.8 g of light brown solid, m.p. 183°–184°. This material was converted to the hydrochloride salt and recrystallized twice from methanol/ether to give 3.5 g of orange needles, m.p. 300°–302° (dec.).

ANALYSIS:

Calculated for $C_{13}H_{10}N_4O_2 \cdot HCl$: 53.71%C 3.81%H 19.28%N

Found: 53.55%C 3.77%H 19.17%N

EXAMPLE 16

N-Methyl-5-nitro-N-(4pyridinyl)-1H-indol-1-amine maleate

A solution of 5-nitro-N-(4-pyridinyl)-1H-indol-1-amine (6 g) in 20 ml of dimethylformamide was slowly added to an ice-cooled NaH suspension prepared by washing 1.2 g of 60% NaH suspension in oil with hexanes and suspending the residue in 5 ml of dimethylformamide. After the anion formation a solution of dimethyl sulfate (3.7 g) in 10 ml of dimethylformamide was added. After one hour the reaction mixture was stirred with water and extracted with ethyl acetate. The organic extract was washed with water and saturated sodium chloride solution, was dried (MgSO$_4$), filtered and concentrated to 6 g of dark oil. This was purified by flash chromatography (silica, ethyl acetate) to give 2.7 g of orange solid., m.p. 149°–150°. This was converted to the maleate salt and recrystallized twice from methanol/ether to give 2.7 g of orange crystals, m.p. 174°–175° (dec.).

ANALYSIS:

Calculated for $C_{14}H_{12}N_4O_2 \cdot C_4H_4O_4$: 56.25%C 4.20%H 14.58%N

Found: 56.14%C 4.27%H 14.46%N

EXAMPLE 17

3-Methyl-N-(4-pyridinyl)-1H-indol-1-amine oxalate

To 200 ml of isopropanol were added 4-chloropyridine hydrochloride (7.5 g) and 3-methyl-1H-indol-1-amine (7.6 g). The mixture was stirred at 90° C. for six hours, and thereafter poured into 400 ml of ice water, and stirred for five minutes. The pH was adjusted to 10 with Na$_2$CO$_3$ solution and then extracted with ethyl acetate. The organic layer was washed with water and dried (saturated NaCl, anhydrous MgSO$_4$). After filtration, the solvent was evaporated to obtain 8.4 g of thick brown oil, which was eluted on a silica gel column with ethyl acetate via HPLC. The desired fractions were combined and concentrated to 7.4 g of brown oil. A 2.3 g sample of this oil was dissolved in 50 ml of ethanol, and the pH adjusted to 1 with an ethanolic solution of oxalic acid, and the solution was diluted with ether. The resultant white precipitate was collected and dried to give 4.0 g, m.p. 130°–135°(dec.). This material was recrystallized from ethanol/ether (1: 1) to give 3.8 g, m.p. 137° (dec.).

ANALYSIS:

Calculated for $C_{14}H_{13}N_3 \cdot C_2H_2O_4$: 61.33%C 4.83%H 13.41%N

Found: 61.41%C 4.96%H 13.28%N

EXAMPLE 18

3-Methyl-N-propyl-N-(4-pyridinyl)-1H-indol-1-amine maleate

To a cold NaH suspension prepared by washing 0.8 g of 60% NaH suspension in oil with hexanes and suspending the residue in 15 ml of dry DMF was added a solution of 3-methyl-N-(4-pyridinyl)-1H-indol-1-amine (4.0 g) in 25 ml of dry. DMF in ten minutes. After ten minutes a solution of propyl bromide (2.7 g) in 15 ml DMF was added. The mixture was stirred at ambient temperature for thirty minutes, poured into 200 ml of ice water, stirred for five minutes, and then extracted with ethyl acetate. The organic layer was washed with water and dried (saturated NaCl, anhydrous MgSO$_4$). After filtration, the solvent was evaporated to give 5 g of brown oil, which was eluted on a silica gel column with ethyl acetate via HPLC. The desired fractions were combined and concentrated to 2.6 g of brown oil. This oil was dissolved in ether, the pH was adjusted to 1 with ethereal maleic acid, and the resultant white precipitate collected and dried to give, 4.0 g, m.p. 148° (dec.). This material was recrystallized from methanol/ether (1: 10) to give 3.5 g of white crystals, m.p. 148°–149°.

ANALYSIS:

Calculated for $C_{17}H_{19}N_3 \cdot C_4H_4O_4$: 66.13%C 6.08%H 11.02%N

Found: 66.15%C 6.02%H 11.00%N

EXAMPLE 19

N-(3-Fluoro-4-pyridinyl)-3-methyl-1H-indol-1-amine

To 200 ml of isopropanol were added 4-chloro-3-fluoropyridine hydrochloride (10 g) and 3-methyl-1 H-indol-amine (5.9 g). The mixture was stirred at 90° C. for four hours, cooled, and poured into 500 ml of ice water. The pH was adjusted to 10 with Na$_2$CO$_3$ solution, and the mixture was extracted with ethyl acetate. The organic layer was washed with water and dried (saturated NaCl, anhydrous MgSO$_4$). After filtration, the solvent was evaporated to give about 10 g of dark oil, which was eluted on a silica gel column first with dichloromethane, and then with ether/petroleum ether (1:1) via "flash chromatography". The desired fractions were combined and concentrated to a yellow solid, 6.2 g, m.p. 45° C. A sample of this material was recrystallized from isopropyl ether/hexanes (1:1) to give a yellow solid, m.p. 141°–142° C.

ANALYSIS:

Calculated for $C_{14}H_{12}FN_3$: 69.69%C 5.02%H 17.42%N

Found: 69.52%C 5.01%H 17.57%N

EXAMPLE 20

N-(3-Fluoro-4-pyridinyl)-N-propyl-3-methyl-1H-indol-1-amine hydrochloride

To a NaH suspension prepared by washing 0.5 g of 60% NaH suspension in oil with hexanes and suspending the residue in 10 ml of DMF, was added a solution of N-(3-fluoro-4-pyridinyl)-3-methyl-1H-indol-1-amine (3.0 g) in 20 ml of DMF at ice-bath temperature in ten minutes. The mixture was stirred for an additional five minutes, and thereafter a solution of propyl bromide (1.2 ml) in 10 ml of DMF was added in five minutes. The mixture was stirred at ambient temperature for thirty minutes, poured into 10 ml of ice-water, and then extracted with ethyl acetate. The organic layer was collected, washed with water, and dried (saturated NaCl, anhydrous $MgSO_4$). After filtration, the solvent was evaporated to give 4 g of brown oil, which was eluted on a silica gel column with 20% ethyl acetate/DCM via HPLC. The desired fractions were combined and concentrated to a thick yellow oil, 3.4 g. The oil was dissolved in ether, the pH adjusted to 1 with ethereal-HCl, and the resultant white precipitate collected and dried to give 3.4 g. This material was recrystallized from ethanol/ether (1:20) to give 2.7 g of white crystals, m.p. 193° (dec.).

ANALYSIS:

Calculated for $C_{17}H_{18}FN_3.HCl$: 63.84%C 5.99%H 13.14%N

Found: 64.11%C 6.01%H 13.20%N

EXAMPLE 21

N-(3-Fluoro-4-pyridinyl)-N-propyl-1H-indol-1-amine hydrochloride

To a NaH suspension prepared by washing 0.6 g of 60% NaH suspension in oil with hexanes and suspending the residue in 10 ml of cold DMF, was added a solution of N-(3-fluoro-4-pyridinyl)-1H-indol-1-amine in 25 ml of DMF. The mixture was stirred at 5° C. for ten minutes, and thereafter a solution of bromopropane (1.4 ml) in 10 ml of DMF was added. The mixture was stirred at ambient temperature for thirty minutes, poured into 200 ml of ice water, stirred for five minutes, and extracted with ethyl acetate. The organic layer was washed with water and dried (saturated NACl, anhydrous $MgSO_4$).

After filtration, the solvent was evaporated to give 3.2 g of brown oil, which was eluted on a silica gel column with 10% ethyl acetate/DCM via HPLC. The desired fractions were combined and concentrated to 2.4 g of brown oil, which was dissolved in 40 ml of absolute ethanol. The pH was adjusted to 1 with ethereal-HCl, and the solution was diluted with 400 ml of ether. The resultant off-white precipitate was collected and dried to give 2.1 g, m.p. 198°–200° (dec.).

ANALYSIS:

Calculated for $C_{16}H_{16}FN_3.HCl$: 62.85%C 5.60%H 13.74%N

Found: 62.80%C 5.60%H 13.66%N

EXAMPLE 22

2-Methyl-N-(4-pyridinyl)-1H-indol-1-amine

The title compound was prepared from 2-methyl-1H-indol-1-amine and 4-chloropyridine hydrochloride at 120° C. for 30 minutes in substantially the same manner as in Example 1, m.p. 75°–78°.

ANALYSIS:

Calculated for $C_{14}H_{13}N_3$: 75.31%C 5,87%H 18.82%N

Found: 75.02%C 5.88%H 18.66%N

EXAMPLE 23

N-(3-Methyl-4-pyridinyl)-1H-indol-1-amine

The title compound was prepared from 1H-indol-1-amine and 4-chloro-3-methylpyridine hydrochloride in isopropanol at 90° C. for 6 hours in substantially the same manner as in Example 1, m.p. 78°–80°.

ANALYSIS:

Calculated for $C_{14}H_{13}N_3$: 75.31%C 5.87%H 18.82%N

Found: 74.98%C 5.83%H 18.86%N

EXAMPLE 24

N-(3-Methyl-4-pyridinyl)-N-propyl-1H-indol-1-amine oxalate

The title compound was prepared from N-propyl-1H-indol-1-amine and 4-chloro-3-methylpyridine hydrochloride in 1-methyl-2-pyrrolidinone at 120° C. for 20 hours in substantially the same manner as in Example 1, m.p. 155° (dec.).

ANALYSIS:

Calculated for $C_{17}H_{19}N_3.C_2H_2O_4$: 64.21%C 5.96%H 11.82%N

Found: 64.15%C 5.85%H 11.69%N

EXAMPLE 25

N-(3-Fluoro-4-pyridinyl-1H-indol-1-amine hydrochloride

The title compound was prepared from 1H-indol-1-amine and 4-chloro-3-fluoropyridine hydrochloride in isopropanol at 90° C. for 4 hours in substantially the same manner as in Example 1, m.p. >250°.

ANALYSIS:

Calculated for $C_{13}H_{10}FN_3.HCl$: 59.21%C 4.21%H 15.93%N

Found: 59.35%C 4.36%H 15.81%N

EXAMPLE 26

N-(3-Chloro-4pyridinyl)-1H-indol-1-amine hydrochloride

The title compound was prepared from 1H-indol-1-amine and 3,4-dichloropyridine hydrochloride in isopropanol at 100° C. for 4 hours in substantially the same manner as in Example 1, m.p. >230°.

ANALYSIS:

Calculated for $C_{13}H_{10}ClN_3.HCl$: 55.73%C 3.96%H 15.00%N

Found: 55.97%C 4.23%H 14.64%N

EXAMPLE 27

N-(3-Fluoro-4-pyridinyl)-2-methyl-1H-indol-1-amine

The title compound was prepared from 2-methyl-1H-indol-1-amine and 4-chloro-3-fluoropyridine hydrochloride in 1-methyl-2-pyrrolidone for 1 hour in substantially the same manner as in Example 1, m.p. 157°–158°.

ANALYSIS:

Calculated for $C_{14}H_{12}FN_3$: 69.69%C 5.02%H 17.42%N

Found: 69.53%C 4.95%H 17.28%N

EXAMPLE 28

N-(3-Chloro-4-pyridinyl)-3-methyl-1H-indol-1-amine hydrochloride

The title compound was prepared from 3-methyl-1H-indol-1-amine and 3,4-dichloropyridine hydrochloride in isopropanol at 80° C. for 5 hours in substantially the same manner as in Example 1. Recrystallized from ethanol, m.p. 278°–280° dec.).

ANALYSIS:

Calculated for $C_{14}H_{12}ClN_3.HCl$: 57.16%C 4.45%H 14.29%N

Found: 57.20%C 4.44%H 14.28%N

EXAMPLE 29

N-Propyl-N-(4-pyridinyl)-1H-indol-1-amine-3-carboxaldehyde maleate

The title compound was prepared from N-propyl-N-(4-pyridinyl)-1H-indol-1-amine, phosphorous oxychloride and dimethylformamide in substantially the same manner as in Example 6, m.p. 169°–171°.

ANALYSIS:

Calculated for $C_{17}H_{17}N_3O.C_4H_4O_4$: 63.79%C 5.35%H 10.63%N

Found: 63.67%C 5.38%H 10.58%N

EXAMPLE 30

N-Propyl-N-(4-pyridinyl)-3-ethenyl-1H-indol-1-amine maleate

The title compound was prepared from N-propyl-N-(4-pyridinyl)-1H-indol-1-amine-3-carboxaldehyde, methyltriphenylphosphonium bromide and potassium-t-butoxide in substantially the same manner as in Example 8. Recrystallized from methanol/ether, m.p. 157°–158° (dec.).

ANALYSIS:

Calculated for $C_{18}H_{19}N_3.C_4H_4O_4$: 67.16%C 5.89%H 10.68%N

Found: 66.87%C 5.76%H 10.56%N

EXAMPLE 31

3-Ethyl-N-propyl-N-(4-pyridinyl)-1H-indol-1-amine maleate

The title compound was prepared by hydrogenating 3-ethenyl-N-propyl-N-(4-pyridinyl)-1H-indol-1-amine in substantially the same manner as in Example 9, m.p. 133°–134°.

ANALYSIS:

Calculated for $C_{18}H_{21}N_3.C_4H_4O_4$: 66.82%C 6.37%H 10.63%N

Found: 66.73%C 6.40%H 10.62%N

EXAMPLE 32

N-Butyl-N-(4-pyridinyl)-1H-indol-1-amine maleate

The title compound was prepared from N-(4-pyridinyl)-1H-indol-1-amine and 1-bromobutane with the aid of NaH in substantially the same manner as in Example 4. Recrystallized from ethanol/ether (1: 10), m.p. 108°–110°. cl ANALYSIS:

Calculated for $C_{17}H_{19}N_3.C_4H_4O_4$: 66.13%C 6.08%H 11.02%N

Found: 66.10%C 6.05%H 11.04%N

EXAMPLE 33

N-(2-Propynyl)-N-(4-pyridinyl)-1H-indol-1-amine maleate

The title compound was prepared from N-(4-pyridinyl)-1H-indol-1-amine and propargyl bromide with the aid of NaH in substantially the same manner as in Example 4. Recrystallized from ethanol/ether, m.p. 107°–109°.

ANALYSIS:

Calculated for $C_{16}H_{13}N_3.C_4H_4O_4$: 66.11%C 4.72%H 11.56%N

Found: 66.04%C 4.69%H 11.45%N

EXAMPLE 34

N-(2-Methylpropyl)-N-(4-pyridinyl)-1H-indol-1-amine maleate

The title compound was prepared from N-(4-pyridinyl)-1H-indol-1-amine and 1-bromo-2-methylpropane with the aid of NaH in substantially the same manner as in Example 4, m.p. 101°–103° C.

ANALYSIS:

Calculated for $C_{17}H_{19}N_3.C_4H_4O_4$: 66.13%C 6.08%H 11.02%N

Found: 66.03%C 6.09%H 11.01%N

EXAMPLE 35

N-Pentyl-N-(4-pyridinyl)-1H-indol-1-amine maleate

The title compound was prepared from N-(4-pyridinyl)-1H-indol-1-amine and 1-bromopentane with the aid of NaH in substantially the same manner as in Example 4. Recrystallized from ethanol/ether (1:9), m.p. 91°–93° C.

ANALYSTS:

Calculated for $C_{18}H_{21}N_3.C_4H_4O_4$: 66.82%C 6.37%H 10.63%N

Found: 66.70%C 6.29%H 10.55%N

EXAMPLE 36

N-(1-Methylpropyl)-N-(4-pyridinyl)-1H-indol-1-amine maleate

The title compound was prepared from N-(4-pyridinyl)-1H-indol-1-amine and 2-bromobutane with the aid of NaH in substantially the same manner as in Example 4. Recrystallized from ethanol/ether, m.p. 117°–118° C.

ANALYSIS:

Calculated for $C_{17}H_{19}N_3.C_4H_4O_4$: 66.13%C 6.08%H 11.02%N

Found: 65.78%C 5.97%H 10.98%N

EXAMPLE 37

N-(1-Methylethyl)-N-(4pyridinyl)-1H-indol-1-amine maleate

The title compound was prepared from N-(4-pyridinyl)-1H-indol-1-amine and 2-bromopropane with the aid of NaH in substantially the same manner as in Example 4. Recrystallized from methanol/ether, m.p. 121°–123°.

ANALYSIS:

Calculated for $C_{16}H_{17}N_3 \cdot C_4H_4O_4$: 65.38%C 5.76%H 11.44%N
Found: 65.28%C 5.81%H 11.36%N

EXAMPLE 38

2-Methyl-N-propyl-N-(4-pyridinyl)-1H-indol-1-amine maleate

The title compound was prepared from 2-methyl-N-(4-pyridinyl)-1H-indol-1-amine and 1-bromopropane with the aid of NaH in substantially the same manner as in Example 4, m.p. 155°–156° (dec.).

ANALYSIS:

Calculated for $C_{17}H_{19}N_3 \cdot C_4H_4O_4$: 66.13%C 6.08%H 11.02%N
Found: 65.78%C 6.08%H 10.82%N

EXAMPLE 39

N-(3-Fluoro-4-pyindyl)-N-(2-propenyl)-3-methyl-1H-indol-1-amine hydrochloride

The title compound was prepared from N-(3-fluoro-4-pyridinyl)-3-methyl-1H-indol-1-amine and allyl bromide with the aid of NaH in substantially the same manner as in Example 4, m.p. 185°–187°.

ANALYSIS:

Calculated for $C_{17}H_{16}FN_3 \cdot HCl$: 64.25%C 5.39%H 13.22%N
Found: 64.15%C 5.39%H 13.08%N

EXAMPLE 40

N-(3-Chloro-4-pyridinyl)-N-propyl-1H-indol-1-amine hydrochloride

The title compound was prepared from N-(3-chloro-4-pyridinyl)-1H-indol-1-amine and propyl bromide with the aid of NaH in substantially the same manner as in Example 4, m.p. 202° C. (dec.).

ANALYSIS:

Calculated for $C_{16}H_{16}ClN_3 \cdot HCl$: 59.63%C 5.32%H 13.04%N
Found: 60.01%C 5.31%H 12.94%N

EXAMPLE 41

N-(3-Fluoro-4-pyridinyl)-N-(2-propynyl)-1H-indol-1-amine hydrochloride

The title compound was prepared from N-(3-fluoro-4-pyridinyl)-1H-indol-1-amine and propargyl bromide with the aid of NaH in substantially the same manner as in Example 4. Recrystallized from methanol/ether (1:5), m.p. 211°–212°.

ANALYSIS:

Calculated for $C_{16}H_{12}FN_3 \cdot HCl$: 63.68%C 4.34%H 13.93%N
Found: 63.46%C 4.20%H 13.72%N

EXAMPLE 42

N-(3-Fluoro-4-pyridinyl)-3-methyl-N-(2-propynyl)-1H-indol-1-amine hydrochloride

The title compound was prepared from N-(3-fluoro-4-pyridinyl)-3-methyl-1H-indol-1-amine and propargyl bromide with the aid of NaH in substantially the same manner as in Example 4. Recrystallized from methanol/ether (1:5), m.p. 206°–207°.

ANALYSIS:

Calculated for $C_{17}H_{14}FN_3 \cdot HCl$: 64.66%C 4.79%H 13.30%N
Found: 64.49%C 4.70%H 13.18%N

EXAMPLE 43

N-(3-Fluoro-4-pyridinyl)-2-methyl-N-propyl-1H-indol-1-amine

The title compound was prepared from N-(3-fluoro-4-pyridinyl)-2-methyl-1H-indol-1-amine and 1-bromopropane with the aid of NaH in substantially the same manner as in Example 4, m.p. 5° C.

ANALYSIS:

Calculated for $C_{17}H_{18}FN_3$: 72.06%C 6.40%H 14.83%N
Found: 71.76%C 6.51%H 14.48%N

EXAMPLE 44

N-(3-Chloro-4-pyridinyl)-3-methyl-N-propyl-1H-indol-1-amine

The title compound was prepared from N-(3-chloro-4-pyridinyl)-3-methyl-1H-indol-1-amine and 1-bromopropane with the aid of NaH in substantially the same manner as in Example 4, m.p. 68°–70°.

ANALYSIS:

Calculated for $C_{17}H_{18}ClN_3$: 68.10%C 6.05%H 14.02%N
Found: 67.99%C 6.01%H 14.01%N

EXAMPLE 45

N-(3-Fluoro-4-pyridinyl)-N-(2-propenyl)-1H-indol-1-amine hydrochloride

To a cold solution of N-(3-fluoro-4-pyridinyl)-1H-indol-1-amine (2.9 g) in 70 ml of dry THF was added potassium t-butoxide (1.7 g), and the mixture was stirred at 0° C. for ten minutes. To this was added a solution of allyl bromide (1.3 ml) in 10 ml of THF. After stirring at 0° C. for 2 hours, the mixture was poured into 100 ml water, stirred for 5 minutes and extracted with ethyl acetate (3x). The organic layer was washed with water and dried (saturated NaCl, anhydrous MgSO4). After filtering, the filtrate was concentrated to an oil, 3.0 g, which was eluted on a silica gel column with 50% ethyl acetate/DCM via HPLC. The desired fractions were combined and concentrated to an oil, 2.0 g, which was dissolved in ethanol. The pH was adjusted to 1 with ethereal HCl, and the solution was diluted with ether. The resultant precipitate was collected and dried to give 2.0 g, m.p. 204°–205°.

ANALYSIS:

Calculated for $C_{16}H_{14}FN_3 \cdot HCl$: 63.26%C 4.98%H 13.83%N
Found: 63.25%C 4.98%H 13.70%N

We claim:

1. A method of alleviating an obsessive compulsive disorder which comprises administering to a patient suffering from an obsessive compulsive disorder an effective amount of a compound depicted below,

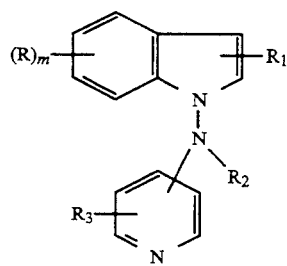

where m is 1 or 2;

R is H, halogen, loweralkyl, loweralkoxy, aryl-loweralkoxy, hydroxy, nitro, amino, loweralkylamino or diloweralkylamino;

$R_1$ is H or loweralkyl;

$R_2$ is H or loweralkyl; and $R_3$ is H, halogen or loweralkyl, or a pharmaceutically acceptable acid addition salt thereof.

2. The method as defined in claim 1, where m is 1.

3. The method as defined in claim 1, where m is 1 and R is hydrogen.

4. The method as defined in claim 1, where $R_2$ is loweralkyl.

5. The method as defined in claim 2, where $R_2$ is loweralkyl.

6. The method as defined in claim 3, where $R_2$ is loweralkyl.

7. The method as defined in claim 1, where $R_1$ is loweralkyl.

8. The method as defined in claim 2, where $R_1$ is loweralkyl.

9. The method as defined in claim 3, where $R_1$ is loweralkyl.

10. The method as defined in claim 1, where $R_3$ is halogen.

11. The method as defined in claim 2, where $R_3$ is halogen.

12. The method as defined in claim 3, where $R_3$ is halogen.

13. The method as defined in claim 1, where $R_1$ is loweralkyl, $R_2$ is loweralkyl and $R_3$ is halogen.

14. The method as defined in claim 2, where $R_1$ is loweralkyl, $R_2$ is loweralkyl and $R_3$ is halogen.

15. The method as defined in claim 3, where $R_1$ is loweralkyl, $R_2$ is loweralkyl and $R_3$ is halogen.

16. The method as defined in claim 13, where $R_3$ is fluorine.

17. The method as defined in claim 14, where $R_3$ is fluorine.

18. The method as defined in claim 15, where $R_3$ is fluorine.

19. The method as defined in claim 18, where $R_2$ is propyl.

20. The method as defined in claim 18, where $R_1$ is 2-methyl.

* * * * *